(12) United States Patent
Han et al.

(10) Patent No.: US 11,793,673 B2
(45) Date of Patent: Oct. 24, 2023

(54) IMPLANT DEVICE FOR EYE DISEASE FOR ADJUSTING INTRAOCULAR PRESSURE

(71) Applicant: MICROT INC., Seoul (KR)

(72) Inventors: Jong Chul Han, Seoul (KR); Chang Won Kee, Seoul (KR)

(73) Assignee: MICROT INC., Seoul (KR)

( * ) Notice: Subject to any disclaimer, the term of this patent is extended or adjusted under 35 U.S.C. 154(b) by 101 days.

(21) Appl. No.: 16/955,414

(22) PCT Filed: Dec. 20, 2018

(86) PCT No.: PCT/KR2018/016301
§ 371 (c)(1),
(2) Date: Jun. 18, 2020

(87) PCT Pub. No.: WO2019/124998
PCT Pub. Date: Jun. 27, 2019

(65) Prior Publication Data
US 2020/0345550 A1    Nov. 5, 2020

(30) Foreign Application Priority Data
Dec. 20, 2017    (KR) .......................... 10-2017-0176208

(51) Int. Cl.
*A61F 9/007*        (2006.01)
*A61M 25/00*        (2006.01)

(52) U.S. Cl.
CPC .. *A61F 9/00781* (2013.01); *A61F 2210/0004* (2013.01); *A61F 2250/0031* (2013.01);
(Continued)

(58) Field of Classification Search
CPC .................. A61F 9/00781; A61F 9/007; A61F 2210/0004; A61F 2250/0031;
(Continued)

(56) References Cited

U.S. PATENT DOCUMENTS

2004/0215126 A1* 10/2004 Ahmed ............... A61F 9/00781
604/9
2007/0191863 A1*  8/2007 De Juan, Jr. .......... A61F 9/0008
606/108
(Continued)

FOREIGN PATENT DOCUMENTS

KR    1020170058811    5/2017
MA          38581 A1 *  4/2016    ......... A61F 9/00781
(Continued)

OTHER PUBLICATIONS

International Search Report (with English translation) and Written Opinion of the International Searching Authority in International Application No. PCT/KR2018/016301, dated Mar. 26, 2019 (11 pages).

*Primary Examiner* — Erich G Herbermann
*Assistant Examiner* — Kate Elizabeth Strachan
(74) *Attorney, Agent, or Firm* — McNeill Baur PLLC

(57) ABSTRACT

The present invention relates to an implant device for an eye disease for adjusting intraocular pressure. An implant device for an eye disease for adjusting the intraocular pressure according to an embodiment of the present invention comprises: a first tube into which the aqueous humor flows so as to adjust the intraocular pressure; and a second tube formed inside the first tube. The second tube is made of a biodegradable material configured to be degraded inside the eye over a predetermined period of time after being inserted into the eye. The first tube and the second tube may be divided into a first area and a second area according to the distance from the anterior chamber of the eyeball. The second area of the first tube and the second tube may have such a structure that the diameter thereof is larger than that of the first area of the first tube and the second tube, and the same can expand as the aqueous humor flows in.

7 Claims, 6 Drawing Sheets

(52) U.S. Cl.
CPC ................ *A61F 2250/0039* (2013.01); *A61M 2025/0004* (2013.01)

(58) Field of Classification Search
CPC ......... A61F 2250/0039; A61M 27/002; A61M 2025/0004; A61M 2210/0612
See application file for complete search history.

(56) References Cited

U.S. PATENT DOCUMENTS

| | | |
|---|---|---|
| 2011/0166535 A1 | 7/2011 | Hasegawa et al. |
| 2014/0236066 A1 | 8/2014 | Horvath et al. |
| 2014/0343476 A1* | 11/2014 | Penhasi ............... A61F 9/00781 604/8 |
| 2015/0148729 A1* | 5/2015 | Pinchuk ............... A61M 27/002 604/8 |
| 2017/0224535 A1 | 8/2017 | Maruyama |
| 2017/0348149 A1* | 12/2017 | Stergiopulos ....... A61M 27/002 |
| 2019/0142631 A1 | 5/2019 | Calhoun et al. |

FOREIGN PATENT DOCUMENTS

| | | |
|---|---|---|
| WO | WO-2016109639 A2 | 7/2016 |
| WO | WO-2017087713 A1 | 5/2017 |
| WO | WO-2017156530 A1 | 9/2017 |

* cited by examiner

IMPLANT DEVICE FOR EYE DISEASE FOR ADJUSTING INTRAOCULAR PRESSURE

CROSS-REFERENCE TO RELATED APPLICATIONS

This application is a national phase entry pursuant to 35 U.S.C. § 371 of International Application No. PCT/KR2018/016301 filed Dec. 20, 2018, which claims the benefit of priority to Korean Application No. 10-2017-0176208 filed Dec. 20, 2017, the entire contents of both of which are incorporated by reference herein for all purposes.

TECHNICAL FIELD

This disclosure relates to an implant device for an eye disease for adjusting an intraocular pressure, and more particularly, to an implant device having a double structure for effectively discharging aqueous humor of a patient who suffers from an eye disease such as glaucoma and made of a material that may be degraded in the eye over time.

BACKGROUND ART

Glaucoma is a disease that causes abnormalities in the function of the optic nerve as the optic nerve is pressed or the blood supply is impaired due to an increase in intraocular pressure. Since the optic nerve is a nerve that transmits the light received by the eye to the brain to make vision, if a disorder occurs in the optic nerve, a visual field is defected, and at the end, vision is lost. The main cause of glaucoma is damage to the optic nerve caused by the increase in intraocular pressure. The intraocular pressure is primarily determined by the aqueous humor (referring to the water produced in the eye, responsible for maintaining the shape of the eye and providing nutrients inside the eye).

The glaucoma treatment includes a drug treatment method in which an intraocular pressure lowering agent is dropped in the eye or taken by a patient, and a glaucoma filtration method in which a small hole is perforated in the s using a laser to help circulate and discharge of the aqueous humor. When the drug treatment method or the glaucoma filtration method is failed or after the glaucoma filtration method is performed, in order to prevent the intraocular pressure from increasing further, a surgery is performed to insert an implant device to maintain intraocular pressure at a constant level by adjusting the amount of aqueous humor n the eye.

Conventional implant devices inserted into the eyeball through a surgery as described above are mostly tube-shaped devices formed of silicon with a diameter of a certain size. Since the implant device has a diameter of a certain size, once being inserted into the eyeball, a constant amount of aqueous humor is continuously discharged regardless of the intraocular pressure, which makes it difficult to effectively control the intraocular pressure.

In addition, in order to stably fix the implant device in the eye, Korean Patent Publication No. 10-2017-0058811 discloses an implant device having a protrusion formed on the outer surface thereof and having an """⊤"" " shape. If the implant device is formed as above, eyeball tissue may be injured while the implant device is being inserted therein. Also, due to the """⊤"" " shape, the aqueous humor may not be effectively discharged.

DISCLOSURE

Technical Problem

This disclosure is to solve the problems as above, and the present disclosure is directed to providing an implant device for an eye disease, which may adjust a discharge amount of aqueous humor generated in the anterior chamber of the eyeball over time in order to effectively treat the eye disease.

In addition, the present disclosure is directed to providing an implant device for an eye disease, which is configured to be stably fixed in the eye in order to prevent problems caused by disengagement of the implant device and efficiently discharge an aqueous humor.

Technical Solution

An implant device for an eye disease for adjusting an intraocular pressure according to an embodiment of the present disclosure may include a first tube into which the aqueous humor flows so as to adjust the intraocular pressure, and a second tube formed inside the first tube, wherein the second tube may be made of a biodegradable material configured to be degraded inside the eye over a predetermined period of time after being inserted into the eye, the first tube and the second tube may be divided into a first area and a second area according to the distance from the anterior chamber of the eyeball, respectively, and the second areas of the first tube and the second tube may have a diameter greater than the first areas of the first tube and the second tube and have an expandable structure as the aqueous humor flows in.

The first areas of the first tube and the second tube according to an embodiment of the present disclosure may have a circular section, and the second areas of the first tube and the second tube may have an oval section.

The first area of the first tube according to an embodiment of the present disclosure may have a diameter of 100 μm or above, and the first area of the second tube may have a diameter in the range of 30 μm or above and less than 100 μm.

The first areas of the first tube and the second tube according to an embodiment of the present disclosure may have a length in the range of 7 mm or above and 10 mm or below.

The second tube according to an embodiment of the present disclosure may further include a rear tube connected to the second area of the second tube and having a diameter equal to or smaller than that of the first area of the second tube, and the first tube may further include a rear protection tube connected to the second area of the first tube and formed to surround the rear tube at the outside thereof to protect the rear tube.

Advantageous Effects

If the implant device for an eye disease according to an embodiment of the present disclosure is used, since the tube inside the device is degraded over time, it is possible to adjust the discharge amount of aqueous humor generated in the anterior chamber of the eyeball, thereby effectively treating the eye disease.

In addition, since a portion of the tube is configured to expand according to the introduction of the aqueous humor, the internal pressure of the tube caused by the introduction of the aqueous humor may be adjusted to efficiently discharge the aqueous humor. Also, since the tube may be fixed without moving inside the eye, the stability of the device may be secured.

BEST MODE

Figure 1:
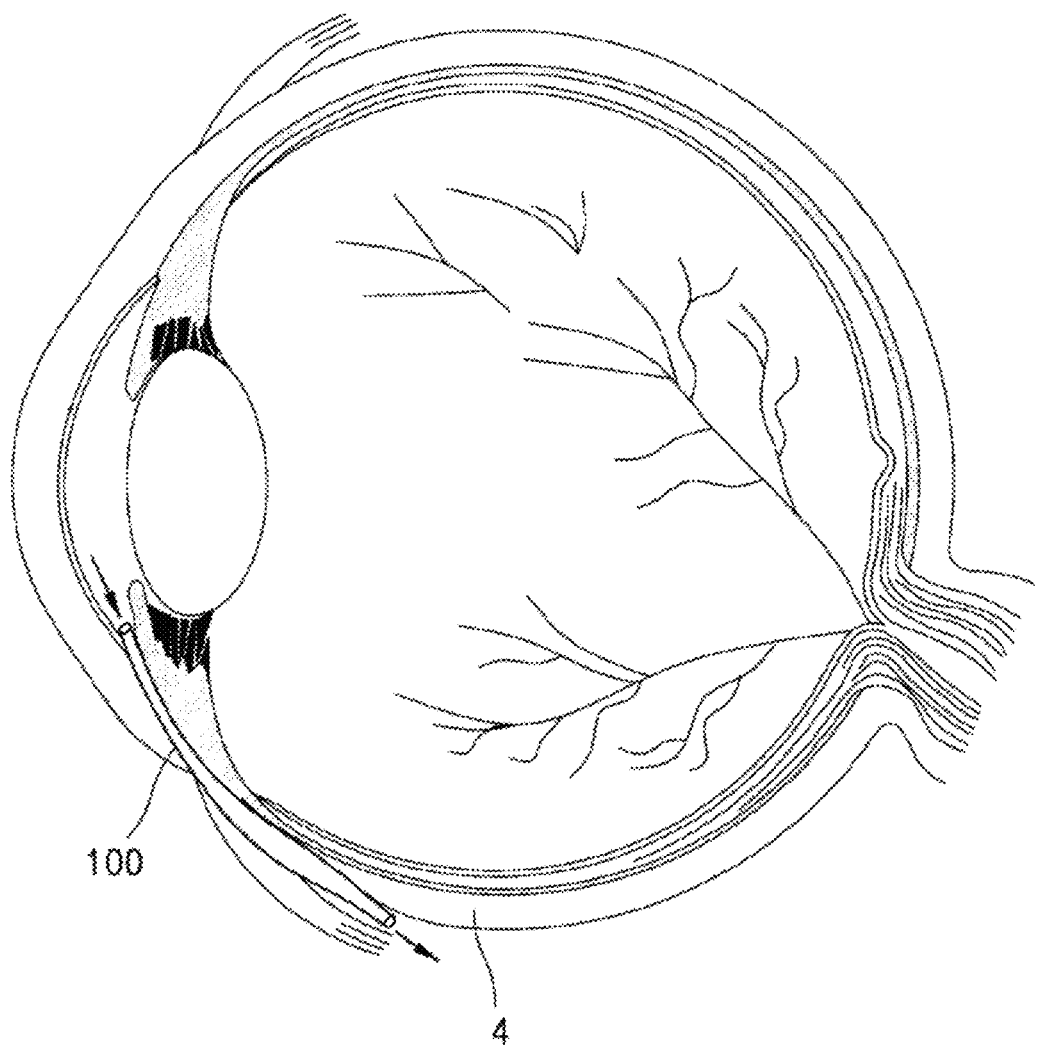
FIG. 1 shows an example in which an implant device for an eye disease according to an embodiment of the present disclosure is inserted into the eye to discharge an aqueous humor.

An implant device for an eye disease for adjusting an intraocular pressure according to an embodiment of the present disclosure may include a first tube into which the aqueous humor flows so as to adjust the intraocular pressure, and a second tube formed inside the first tube, wherein the second tube may be made of a biodegradable material configured to be degraded inside the eye over a predetermined period of time after being inserted into the eye, the first tube and the second tube may be divided into a first area and a second area according to the distance from the anterior chamber of the eyeball, respectively, and the second areas of the first tube and the second tube may have a diameter greater than the first areas of the first tube and the second tube and have an expandable structure as the aqueous humor flows in.

The first areas of the first tube and the second tube according to an embodiment of the present disclosure may have a circular section, and the second areas of the first tube and the second tube may have an oval section.

The first area of the first tube according to an embodiment of the present disclosure may have diameter of 100 µm or above, and the first area of the second tube may have a diameter in the range of 30 µm or above and less than 100 µm.

The first areas of the first tube and the second tube according to an embodiment of the present disclosure may have a length in the range of 7 mm or above and 10 mm or below.

The second tube according to an embodiment of the present disclosure may further include a rear tube connected to the second area of the second tube and having a diameter equal to or smaller than that of the first area of the second tube, and the first tube may further include a rear protection tube connected to the second area of the first tube and formed to surround the rear tube at the outside thereof to protect the rear tube.

Mode for Invention

Terms used in this specification will be briefly described, and the present disclosure will be described in detail.

The terms used in the present disclosure are selected from general terms as widely used as possible at present while considering the functions in the present disclosure, but they may vary depending on the intention or precedent of a person skilled in the art or the appearance of new technologies. In addition, in certain cases, some terms are arbitrarily selected by the applicant, and in this case, their meanings will be described in detail in the following description. Therefore, the terms used in the present disclosure should be defined based on the meanings of the terms and the contents throughout the present disclosure, not just on the names of the terms.

When a part of the specification "includes" a certain component, this means that other components may be further included therein, instead of excluding other components, unless specifically stated to the contrary. In addition, a term such as " . . . unit" and " . . . module" described in the specification means a unit that processes at least one function or operation, which may be implemented in hardware or software, or a combination of hardware and software.

Hereinafter, an embodiment of the present disclosure will be described in detail with reference to the accompanying drawings so as to be easily implemented by those skilled in the art. However, the present disclosure can be implemented in many different forms and is not limited to the embodiments described herein. In addition, for clear explanation, parts irrelevant to the description are omitted, and like reference numerals are assigned to like components throughout the specification.

Hereinafter, the present disclosure will be described in detail with reference to the accompanying drawings.

FIG. 1 shows an example in which an implant device for an eye disease according to an embodiment of the present disclosure is inserted into the eye to discharge an aqueous humor.

The implant device 100 for an eye disease according to an embodiment of the present disclosure refers to a tube-type implant device for controlling an intraocular pressure by adjusting the amount of aqueous humor generated in an anterior chamber (anterior chamber) of the eyeball in order to prevent the optic nerve from being damaged by the intraocular pressure increased due to the eye disease. The implant device 100 for an eye disease may be inserted by peeling off a conjunctival tissue or tenon tissue 4 of the eyeball, and after being inserted, the implant device 100 may be placed in the eye by covering the conjunctival tissue or tenon tissue 4 again. Referring to FIG. 1, when the implant device 100 for an eye disease is inserted, one side of the device is inserted into the anterior chamber of the eyeball (i.e., the intraocular in the eyeball), and the other side may be inserted into the conjunctival tissue or tenon tissue 4 (i.e., an upper side of the sclera outside the eyeball, extraocular). By doing so, the aqueous humor generated in the anterior chamber may be discharged to the conjunctival tissue or tenon tissue 4 through the implant device 100 for an eye disease.

According to an embodiment of the present disclosure, the eye disease may include glaucoma caused by an increase in intraocular pressure, and the glaucoma may include congenital glaucoma, traumatic glaucoma, glaucoma suspected, high intraocular pressure, primary open-angle glaucoma, normal intraocular pressure glaucoma, lens cystic glaucoma with pseudo-snowfall of the lens, chronic simple glaucoma, low intraocular pressure glaucoma, pigmented glaucoma, primary closed-angle glaucoma, acute closed-angle glaucoma, chronic closed-angle glaucoma, intermittent closed-angle glaucoma, glaucoma secondary to trauma of the eye, glaucoma secondary to inflammation of the eye, glaucoma secondary to drug, neovascular glaucoma, and secondary glaucoma due to uveitis.

Figure 2:
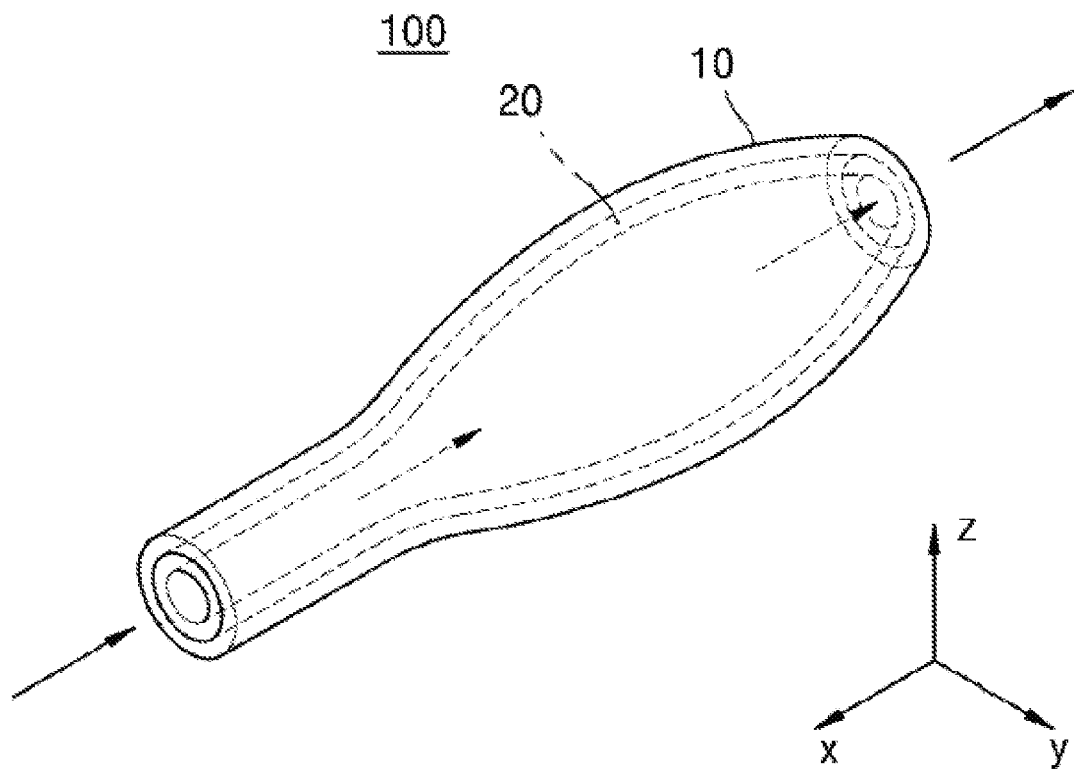
FIG. 2 is a perspective view showing an example of the implant device for an eye disease for adjusting an intraocular pressure according to an embodiment of the present disclosure.

FIG. 2 is a perspective view showing an example of the implant device 100 for an eye disease for adjusting an intraocular pressure according to an embodiment of the present disclosure, and FIGS. 3A to 3D are cross-sectional views showing an example of the implant device 100 for an eye disease for adjusting an intraocular pressure according to an embodiment of the present disclosure.

Referring to FIGS. 2 and 3A to 3D, the implant device 100 for an eye disease for controlling an intraocular pressure according to an embodiment of the present disclosure includes a first tube 10 into which an aqueous humor flows to adjust the intraocular pressure, and a second tube 20 formed inside the first tube 10. Here, the second tube 20 may be formed of a biodegradable material that is degraded in the eye as a predetermined tune passes after being inserted into the eye. In addition, the first tube 10 and the second tube 20 may be divided into a first area 11, 21 and a second area 12, 22 according to the distance from the anterior chamber of the eyeball. Here, the second area 12, 22 of the first tube 10 and the second tube 20 may have a diameter greater than the first area of the first tube 10 and the second tube 20, and may have an expandable structure as the aqueous humor flows in.

When the intraocular pressure needs to be controlled due to an eye disease such as glaucoma, the amount of aqueous humor must be controlled over a period of time so that the intraocular pressure may be efficiently controlled to effectively treat the eye disease such as glaucoma. In order to achieve these objectives and effects, the implant device 100 for an eye disease according to according to an embodiment of the present disclosure include the second tube 20 that is made of a biodegradable material degraded in the eye over a predetermined time and formed at the inside of the first tube 10 that forms the exterior of the device. At this time, the biodegradable material may be collagen, chitin, or the like. Without being limited thereto, the biodegradable material may include all kinds of biodegradable materials that may be degraded in vivo without causing various diseases even after being degraded and with no side effects. In addition, the second tube 20 may be preferably formed to be completely degraded for a month, and the second tube 20 may be formed so that the time required for completely degrading the second tube 20 varies depending on the degree of eye disease and the state of the eyeball.

In addition, the second area 12 of the first tube 10 may be made of a biodegradable material that is degraded in the eye as a predetermined time flows, like the second tube 20 described above. That is, since the first area 11 of the first tube 10 is made of a material that is not degraded, such as silicone, and the second area 12 is made of a biodegradable material such as collagen and chitin, the first area 11 and the second area 12 may be made of different materials. This is to effectively control the intraocular pressure by adjusting the discharge amount of aqueous humor, and the first area 11 of the first tube 10 made of a material that is not degraded may serve as a passage supporting the continuous discharge of the aqueous humor. In addition, if the second area 12 of the first tube 10 is made of a biodegradable material like the second tube 20, the aqueous humor may be controlled more easily since the second areas 12, 22 are degraded as a predetermined time flows, without additional manipulation.

Figure 3A:
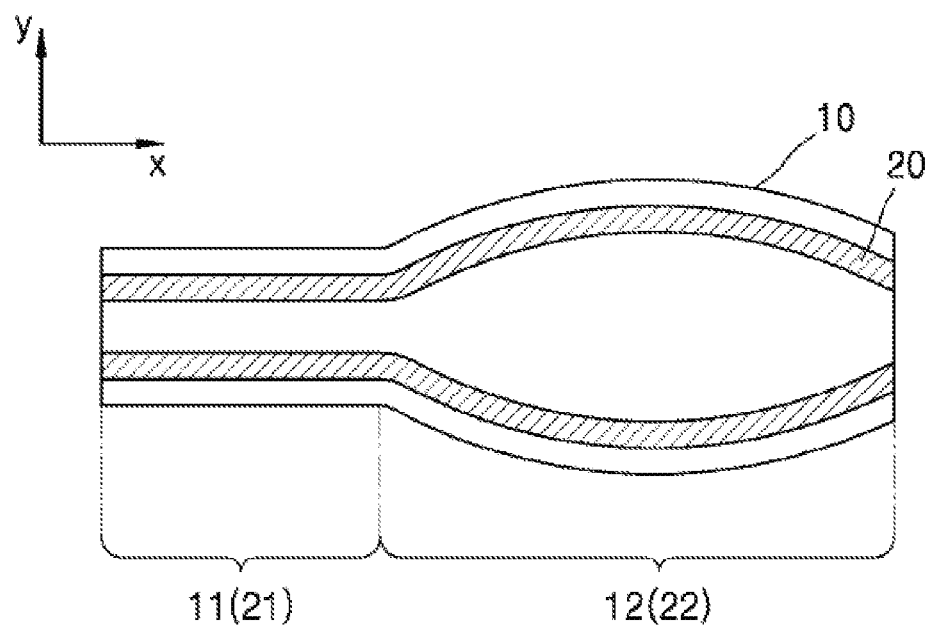
FIGS. 3A to 3D are cross-sectional views showing an example of the implant device for an eye disease for adjusting an intraocular pressure according to an embodiment of the present disclosure.
Figure 3B:
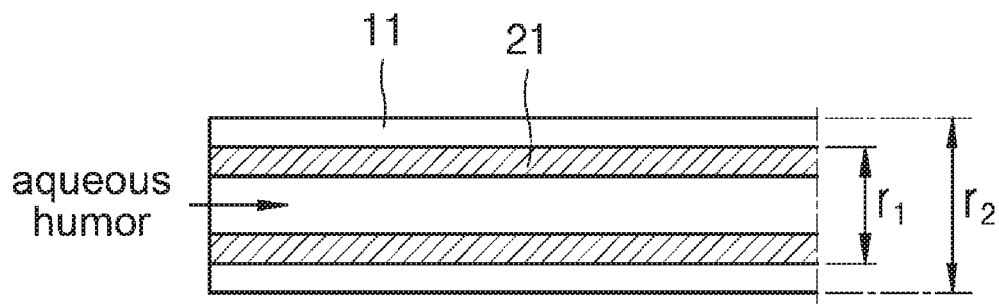
Figure 3C:
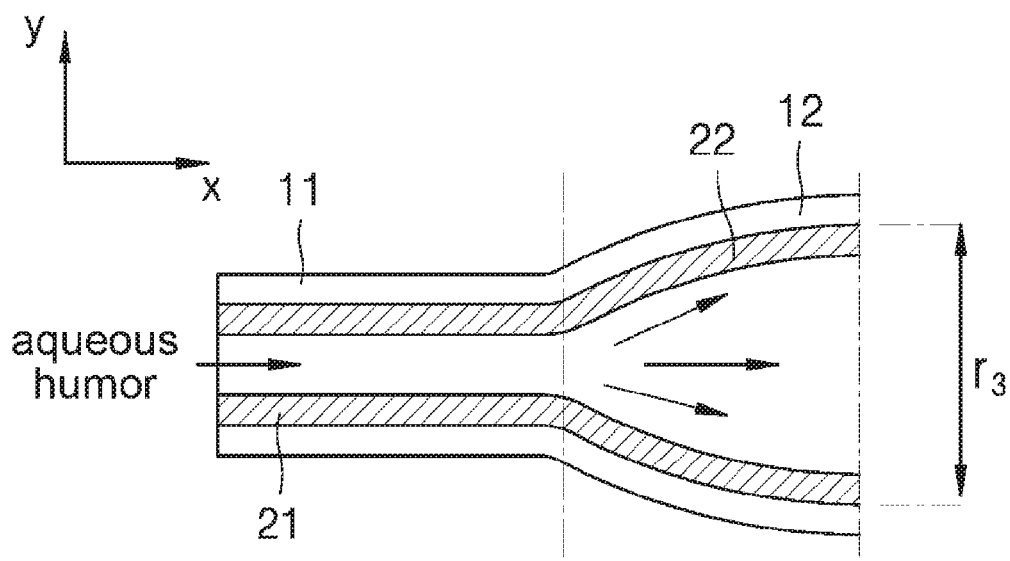

Referring to FIGS. 3B and 3C, an area relatively close to the anterior chamber of the eyeball may be classified into the first area 11, 21, and an area connected to the first area 11, 21 and relatively distant from the anterior chamber of the eyeball may be classified into the second area 12, 22. At this time, the second area 12, 22 is intended to control the pressure of the incoming aqueous humor so that the aqueous humor may be discharged at an appropriate flow speed and flow amount. When the second tube 20 is completely degraded at which the purpose described above has been achieved and the second area 12 of the first tube 10 is no longer needed, the second area 12 of the first tube 10 may be removed by opening the same with a needle or the like by a clinician. After the second area 22 is removed, only the first area 11 of the first tube 10 remains in the eye to discharge a certain amount of aqueous humor, thereby adjusting the intraocular pressure.

FIG. 3A shows a cross-sectional view of the implant tube 100 for an eye disease based on the X-axis and the Y-axis. That is, referring to FIGS. 2 and 3A, the second areas 12, 22 of the first tube 10 and the second tube 20 may be formed to have a greater diameter than the first areas 11, 21 in the Y-axis direction and may have a structure that may be expanded in the Y-axis and Z-axis directions as the aqueous humor flows in.

Figure 3D:
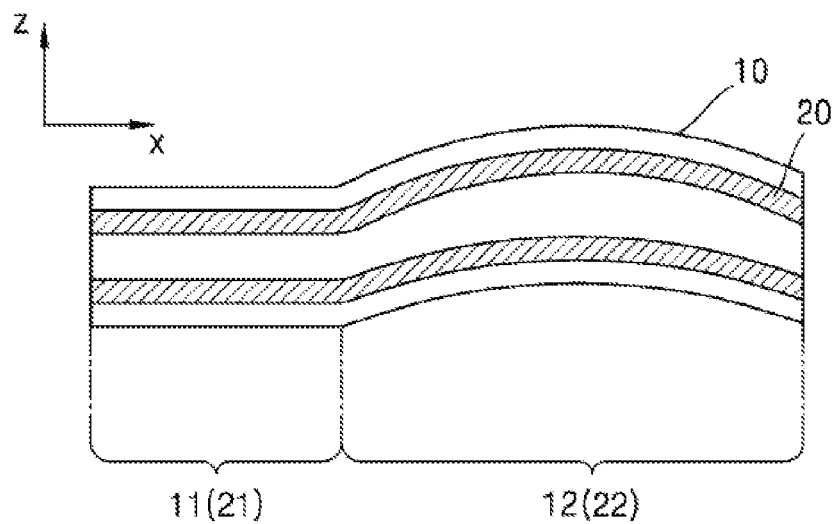

FIG. 3D shows a cross-sectional view based on the X-axis and the Z-axis of the implant tube 100 for an eye disease. Referring to FIG. 3D, one surface of the implant tube 100 for an eye disease according to an embodiment of the present disclosure may be formed to be curved similar to the curved surface of the eyeball. At this time, one surface of the implant tube 100 for an eye disease refers to a portion disposed toward the vitreous humor of the eyeball when the implant tube 100 for an eye disease is inserted into the eye, and thus may be a bottom surface of the second area 11, 22 as shown in FIG. 3D. If one surface of the implant tube 100 is formed similar to the curved surface of the eyeball, the implant tube 100 may be more stably fixed in the eye.

Referring to FIGS. 2 and 3, the first areas 11, 21 of the first tube 10 and the second tube 20 according to an embodiment of the present disclosure may have a circular cross section. In addition, the second areas 12, 22 of the first tube 10 and the second tube 20 may have an oval cross section curved toward an upper portion the tube 100 (i.e. the Z-axis). That is, since the first areas 11, 21 of the tube 100 are formed to have a constant diameter, their cross-section may be formed in a circular shape. In addition, the second area 12, 21 may have a long diameter in the Y-axis direction and a short diameter in the X-axis direction to form an oval shape curved in the Z-axis direction. The second area 12, 21 is formed in an oval shape curved in the Z-axis direction because one surface of the tube 100 (i.e., the bottom surface of the second area 11, 22) has a curved shape similar to the curved surface of the eyeball.

In addition, in order to allow the second areas 12, 22 to be easily expandable in the Z-axis direction, the second areas 12, 22 of the first tube 10 and the second tube 20 may have a relatively small thickness compared to the first areas 11, 21. Since the second areas 12, 22 have an expandable structure to control the pressure inside the tube formed by the introduced aqueous humor, for the purpose that the aqueous humor is fixed and flows to expand the second areas 12, 22, the thickness of the second areas 12, 22 may be relatively smaller compared to the first areas 11, 21 formed to have a predetermined thickness.

According to an embodiment of the present disclosure, a hole may be formed at a contact point between the first area 11 and the second area 12 of the first tube 10, and a medical thread or the like may be connected through the hole to easily fix the implant tube 100 for an eye disease inside the eye. That is, after the implant tube 100 for an eye disease is inserted into the eye, the hole formed by the clinician at the contact point of the first area 11 and the second area 12 of the first tube 10 is connected to the tissue inside the eye through a medical thread or the like, which makes it possible to prevent problems that the implant tube 100 for an eye disease is shaken or moved from the inserted area to another area due to the pressure of the aqueous humor or the fibrous tissue inside the eye.

Referring to FIGS. 3B and 3C, the aqueous humor flows into the first areas 11, 21 and is discharged through the second areas 12, 22. Here, the second areas 12, 22 may have a greater diameter than the first area 11, 21 such that the aqueous humor is effectively discharged using the pressure of the incoming aqueous humor. At this time, the first area 11 of the first tube 10 may have a diameter ($r_2$) of 100 μm or above, and the first area 21 of the second tube 20 may have a diameter ($r_1$) in the range of 30 μm or above and less than 100 μm. Preferably, before being degraded, the first area 21 of the second tube 20 may have a diameter ($r_1$) of 45 μm. As described above, since the diameter of the second areas 12, 22 may be greater than the diameter of the first areas 11, 21, the diameter ($r_3$) of the second area 22 of the second tube 20 may be greater than the diameter ($r_1$) of the first area 11 of the first tube 10.

In addition, outlets of the second area 12, 22 of the first tube 10 and the second tube 20 at which the aqueous humor is discharged may have a diameter equal to or greater than inlets of the first area 11, 21 of the first tube 10 and the second tube 20 at which the aqueous humor is introduced. That is, since the diameter of the outlet determines a flow rate of the aqueous humor that is finally discharged the implant device 100 for an eye disease, the diameters of the outlets of the second areas 12, 22 of the first tube 10 and second tube 20 may be selected to be equal to or greater than the diameters of the inlets of the first areas 11, 21 in order to control the discharge speed and amount of the aqueous humor depending on the degree of the eye disease, the state of the eyeball or the like.

The first areas 11, 21 of the first tube 10 and the second tube 20 according to an embodiment of the present disclosure may have a length in the range of 7 mm or above and 10 mm or below. That is, as described above, after the second area 12 is removed by the clinician or the like, the aqueous humor must be discharged from the anterior chamber of the eyeball to the conjunctival tissue or tenon tissue through only the first area 11. Thus, the first areas 11, 21 may be formed to have a length in the range of 7 mm or above and 10 mm or below in order to stably discharge the aqueous humor.

Although clinical effects may be remarkable within the above numerical ranges (e.g., the aqueous humor is appropriately maintained or discharged), the present disclosure is not necessarily limited to these ranges. The implant device according to the present disclosure lay be manufactured to have a diameter or length predetermined in consideration of the patient's eyeball size, treatment time, period, and the like.

Figure 4:
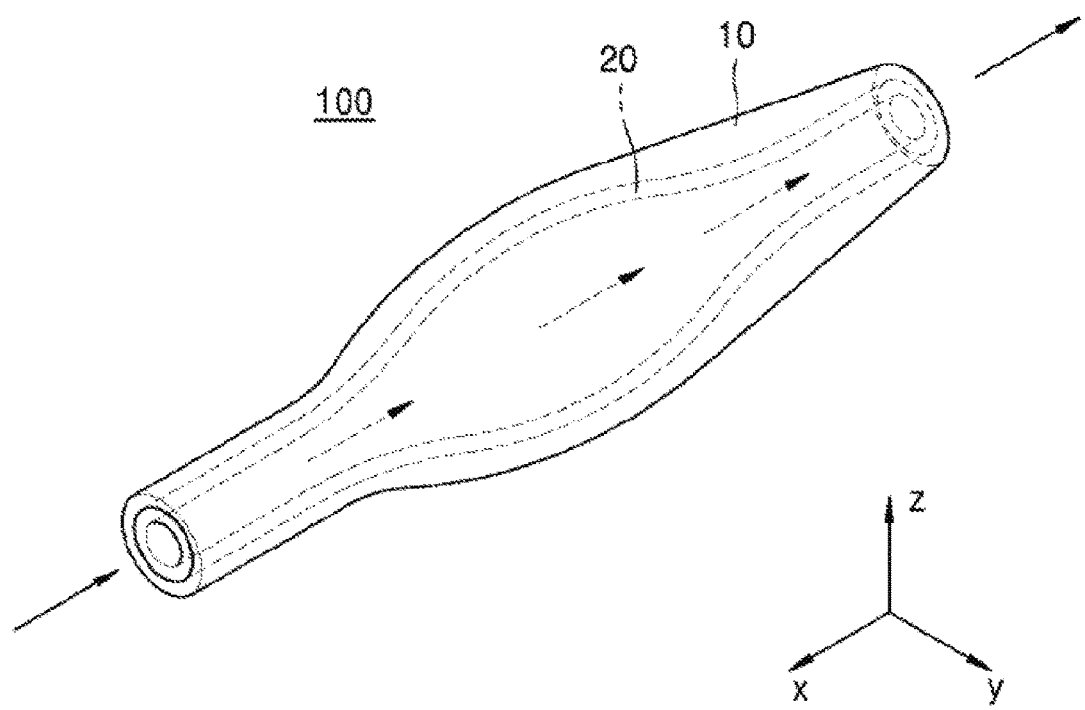
FIG. 4 is a perspective view showing another example of the implant device for an eye disease for adjusting an intraocular pressure according to an embodiment of the present disclosure.
Figure 5A:
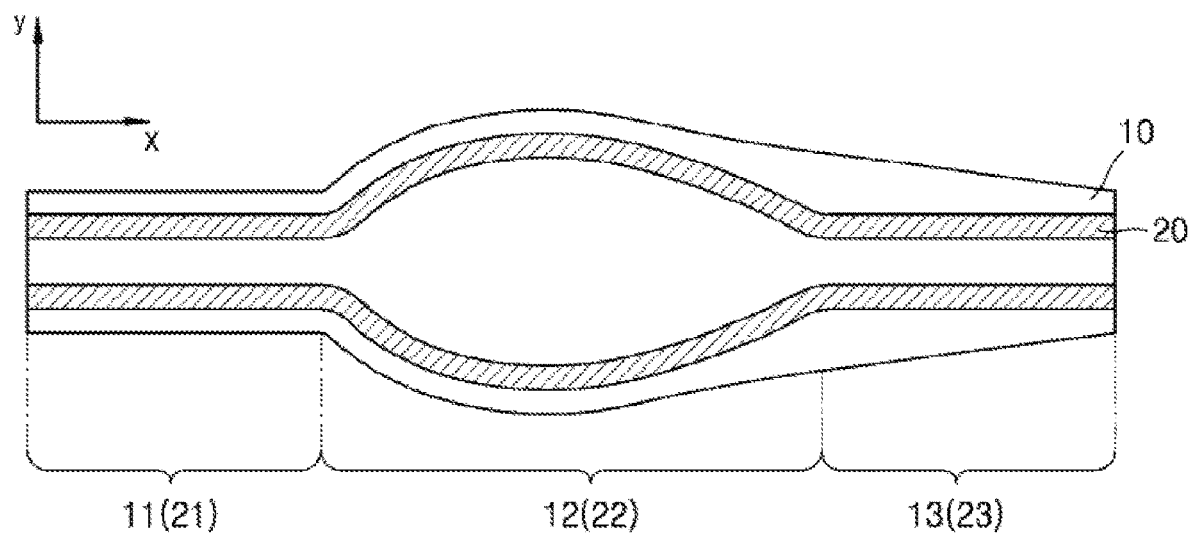
FIGS. 5A to 5C are cross-sectional views showing another example of the implant device for an eye disease for adjusting an intraocular pressure according to an embodiment of the present disclosure.
Figure 5B:
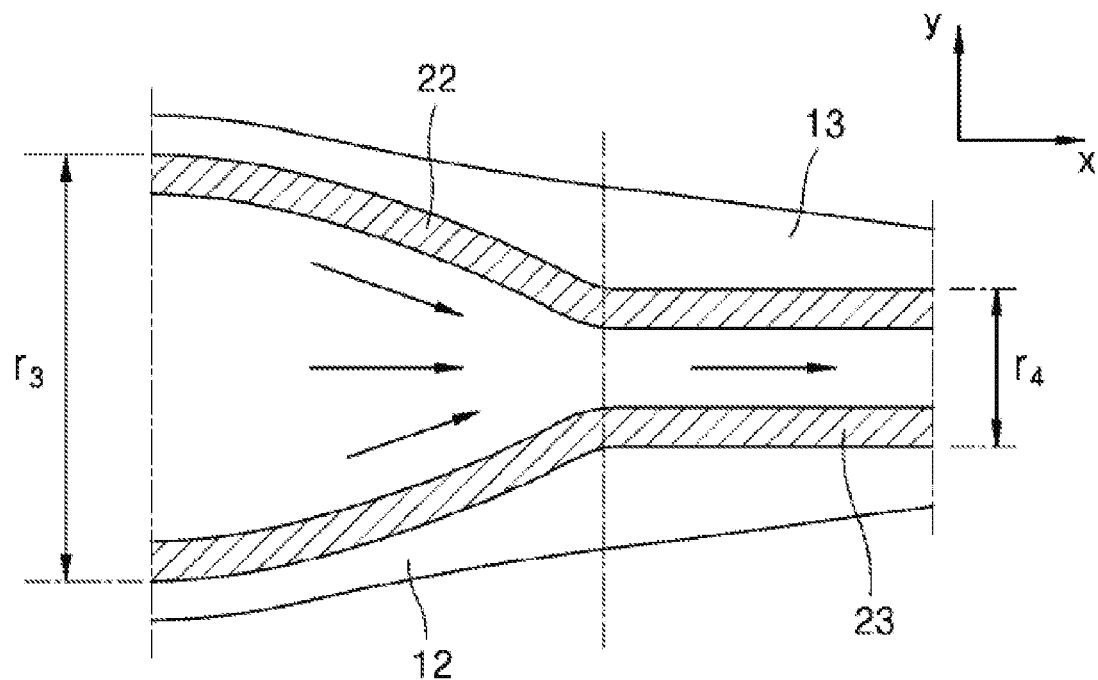
Figure 5C:
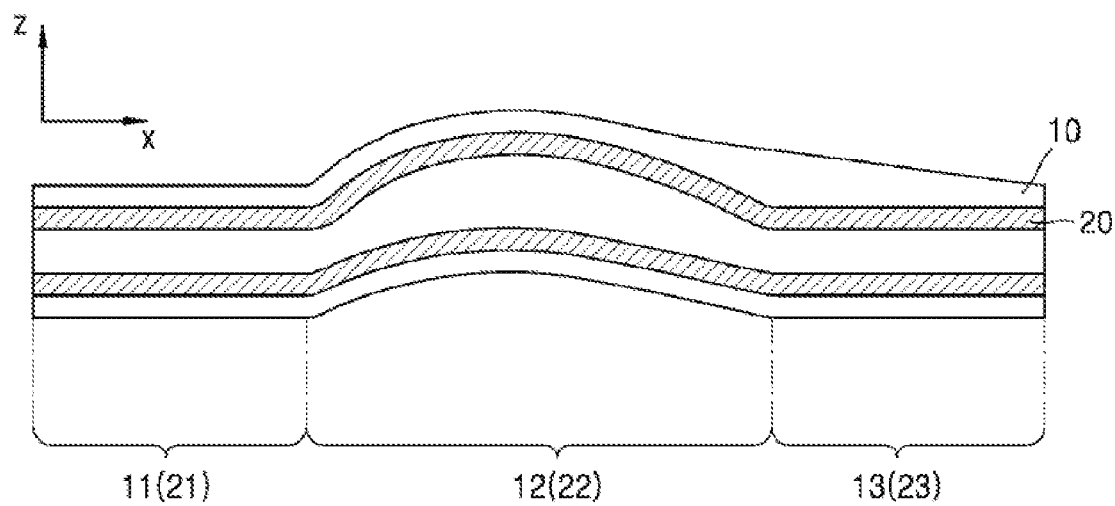

FIG. 4 is a perspective view showing another example of the implant device 100 for an eye disease for adjusting an intraocular pressure according to an embodiment of the present disclosure, and FIGS. 5A to 5C are cross-sectional views showing another example of the implant device 100 for an eye disease for adjusting an intraocular pressure according to an embodiment of the present disclosure.

Referring to FIGS. 4, 5A and 5B, the second tube 20 according to an embodiment of the present disclosure may further include a rear tube 23 connected to the second area 22 of the second tube 20 and formed to have a diameter identical to or smaller than the first area 21 of the second tube 20. In addition, the first tube 10 may further include a rear protection tube 13 connected to the second area 12 of the first tube 10 and formed to surround the tube 23 from the outside to protect the rear tube 23.

In other words, referring to FIG. 5B the rear tube 23 of the second tube 20 is additionally formed to be connected to the second area 22 of the second tube 20 for effective pressure adjustment of the aqueous humor, and the diameter ($r_4$) of the rear tube 23 may be equal to or smaller than the diameter ($r_1$) of the first area 21 of the second tube 20 by determining the discharge amount, the discharge speed or the like of the aqueous humor according to the degree of the eye disease, the state of the eyeball, or the like.

In addition, referring to FIG. 5A, the rear protection tube 13 of the first tube 10 may be formed to surround the rear tube 23 from the outside in order to prevent the case where the rear tube 23 of the second tube 20 is blocked or damaged by the fiber tissue. The rear protection tube 13 is formed to be connected to the second area 12 of the first tube 10 and may be formed to a thickness greater than the second area 12 of the first tube 10 since the rear protection tube 13 is to protect the rear tube 23 from the fibrous tissue. In addition, the rear protection tube 13 and rear tube 23 may be removed when the second tube 20 is completely degraded in the same way as the second area 12, 22 of the first tube 10 and the second tube 20 by opening the same with a needle or the like by a clinician or the like. Even through the rear protection tube 13 and the rear tube 23 are not removed, if the rear protection tube 13 and the rear tube 23 are made of a biodegradable material as described above, they may be naturally degraded as predetermined time flows to easily control the hydraulic pressure and discharge amount of the aqueous humor.

FIG. 5C shows another example of the cross-section of the implant tube 100 for an eye disease based on the X-axis and Z-axis. Referring to FIG. 5C, the implant tube 100 for an eye disease according to an embodiment of the present disclosure may have one surface curved in a shape similar to the curved surface of the eyeball. At this time, one surface of the implant tube 100 for an eye disease refers to a portion disposed toward the vitreous humor of the eyeball when the implant tube 100 for an eye disease is inserted into the eye, and this may be the second areas 12, 22, the bottom surface of the rear tube 23 or the like as shown in FIG. 5C. If one surface of the implant tube 100 is formed in a shape similar to the curved surface of the eyeball, the implant tube 100 may be more stably fixed in the eye.

Figure 6A:
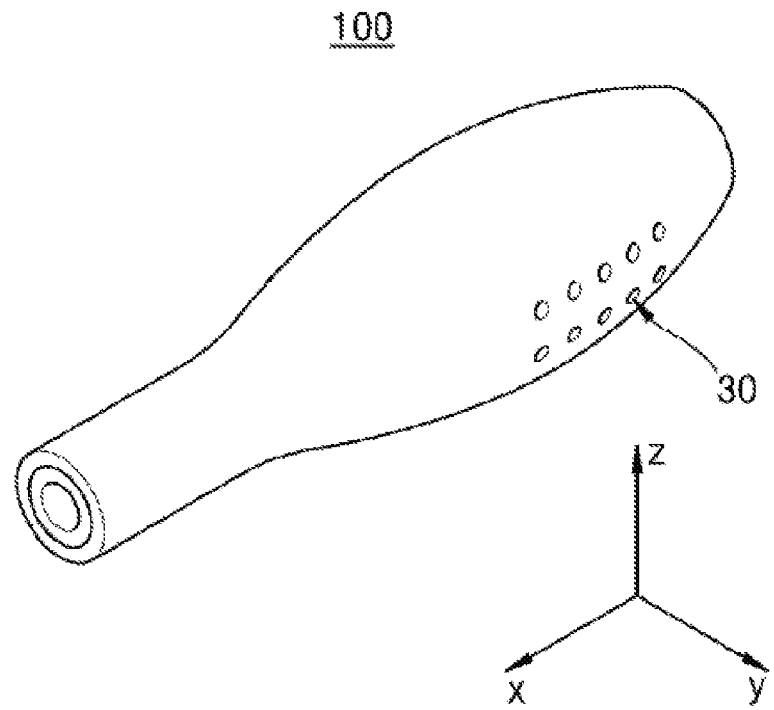
FIGS. 6A and 6B are perspective views showing an implant device for an eye disease for adjusting an intraocular pressure according to an embodiment of the present disclosure in which a pore is formed.
Figure 6B:
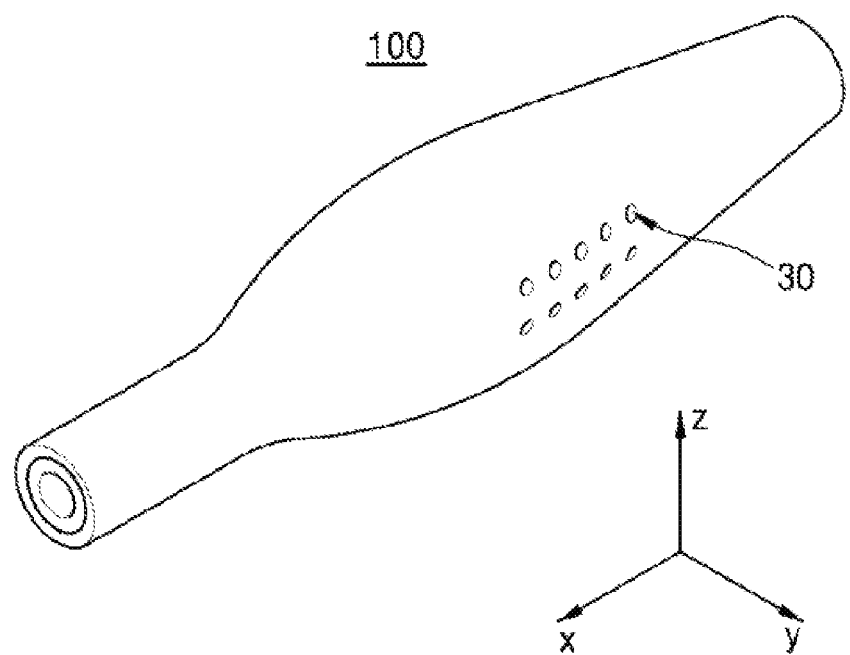

FIGS. 6A and 6B are perspective views g an implant device 100 for an eye disease for adjusting an intraocular pressure according to an embodiment of the present disclosure in which a pore 30 is formed.

Referring to FIG. 6A, a pore 30 for fixing the implant device 100 for an eye disease may be formed in the second area 12 of the first tube 10. That is if the pore 30 is formed in the second area 12 of the first tube 10, after the implant device 100 for an eye disease is inserted into the eye, the fibrous tissue of the eyeball that growing over time may be introduced into the pore 30 to fix the implant device 100 for an eye disease. If the pore 30 is formed in the second tube 20, the fiber tissue may be introduced into the tube and disturb the movement of the aqueous humor. Therefore, the pore 30 is preferably formed in the first tube 10, but may also be formed in the second tube 20 according to the purpose.

In addition, even when the rear tube 23 and the rear protection tube 13 are additionally formed as shown in FIG. 6B, the pore 30 for fixing the implant device 100 for an eye disease may be formed in at least one of the second area 12 and the rear protection tube 13 of the first tube 10. Since the rear protection tube 13 is formed to have a relatively greater thickness to protect the rear tube 23 in comparison to the second area 12 of the first tube 10 as described above, the pore 30 is preferably formed in the rear protection tube 13, without being limited thereto.

The present disclosure is for illustration only, and a person skilled in the art will understood that the present disclosure can be easily modified to other specific forms without changing the technical idea or essential features of the present disclosure. Therefore, it should be understood that the embodiments described above are illustrative in all aspects and not restrictive. For example, each component described as a single type may be implemented in a distributed manner, and similarly, components described as being distributed may be implemented in a combined form.

The scope of the present disclosure is defined by the appended claims, rather than the detailed description, and the meaning and scope of the claims and all altered or modified forms derived from the equivalent concept thereof should be interpreted to be included in the scope of the present disclosure.

The invention claimed is:

1. An implant device for an eye disease for adjusting an intraocular pressure, comprising:
    a first tube, wherein a side of the first tube is configured to be inserted into the anterior chamber of the eyeball such that the aqueous humor flows into the first tube so as to adjust the intraocular pressure and wherein another side of the first tube is configured to be inserted into a conjunctival tissue or a tenon tissue of the eye to discharge the aqueous humor; and
    a second tube formed inside the first tube,
    wherein the second tube is made of a biodegradable material configured to be degraded inside the eye over a predetermined period of time after being inserted into the eye,
    the first tube and the second tube are divided into a first area and a second area, wherein the first area is configured to be closer to the anterior chamber of the eyeball than the second area, and
    the first tube and the second tube are configured such that the aqueous humor is discharged in a first direction,
    the second areas of the first tube and the second tube have a diameter greater than the first areas of the first tube and the second tube, respectively, and have a thickness smaller than the first areas of the first tube and the second tube, respectively, and are configured to be expandable in a direction perpendicular to the first direction as the aqueous humor flows in,
    wherein the second areas of the first tube and the second tube have an oval section such that bottom surfaces of the second areas have a curved shape corresponding to a curved surface of the eyeball,
    wherein outlets of the second areas of the first tube and the second tube at which the aqueous humor is discharged have a diameter greater than inlets of the first areas of the first tube and the second tube at which the aqueous humor is introduced,
    wherein the second tube further comprises a rear tube connected to the second area of the second tube and having a diameter equal to or smaller than that of the first area of the second tube, and the first tube further comprises a rear protection tube connected to the second area of the first tube and formed to surround the rear tube at the outside the rear tube to protect the rear tube,
    wherein the rear protection tube has a thickness greater than a thickness of the second area of the first tube, and
    wherein a pore configured to fix the implant device to fibrous tissue of the eyeball is formed in the rear protection tube.

2. The implant device for an eye disease according to claim 1, wherein the first areas of the first tube and the second tube have a circular section.

3. The implant device for an eye disease according to claim 1, wherein the first area of the first tube has a diameter of 100 μm or above, and the first area of the second tube has a diameter in the range of 30 μm or above and less than 100 μm.

4. The implant device for an eye disease according to claim 1, wherein the first areas of the first tube and the second tube have a length in the range of 7 mm or above and 10 mm or below.

5. The implant device for an eye disease according to claim 1, wherein the pore is formed on a surface of the rear protection tube in a second direction, the second direction being perpendicular to the first direction, and the pore is configured such that fibrous tissue of the eye is introduced into the pore.

6. The implant device for an eye disease according to claim 1, further comprising a hole at a contact point between the first area and the second area of the first tube, wherein the hole is configured to have a medical thread connected through the hole to fix the implant tube for an eye disease inside the eye.

7. The implant device for an eye disease according to claim 1, wherein the first area of the first tube is formed of a material that is not degradable, and the second area of the first tube is formed of a biodegradable material.

* * * * *